United States Patent [19]

Nieh et al.

[11] 4,233,447
[45] Nov. 11, 1980

[54] PROCESS FOR PURIFYING TRIETHYLENEDIAMINE

[75] Inventors: Edward C. Y. Nieh; Kenneth P. Keating, both of Austin, Tex.

[73] Assignee: Texaco Development Corp., White Plains, N.Y.

[21] Appl. No.: 972,098

[22] Filed: Dec. 21, 1978

[51] Int. Cl.$^3$ .................................. C07D 487/00
[52] U.S. Cl. ...................................... 544/352
[58] Field of Search ............... 260/583 N, 583 P; 544/352

[56] References Cited

U.S. PATENT DOCUMENTS

| 3,055,809 | 9/1962 | Lichtenwalter | 260/583 P |
| 3,080,371 | 3/1963 | Spielberger | 544/352 |
| 3,993,651 | 11/1976 | Keating | 544/352 |

Primary Examiner—John F. Niebling
Attorney, Agent, or Firm—Carl G. Ries; Robert A. Kulason; James L. Bailey

[57] ABSTRACT

A process is provided for recovering substantially pure triethylenediamine in liquid lower alkylene diol solutions directly from the crude triethylenediamine reaction mixture without resort to a need to purify the triethylenediamine by crystallization. The process includes initially admixing a lower alkylene diol with a crude triethylenediamine liquid reaction product mixture. The admixture thus formed is then heated to remove water and other low boiling impurities. The crude triethylene diaminediol bottoms mixture is then codistilled to recover a pure triethylene diamine product in diol solvent which can be used directly to catalyze urethane systems.

1 Claim, No Drawings

PROCESS FOR PURIFYING TRIETHYLENEDIAMINE

BACKGROUND OF THE INVENTION

1. Field of the Invention

This invention relates to the recovery of substantially pure triethylenediamine; and more particularly to a process for recovering a triethylenediamine solute in a liquid lower alkylene diol solution directly from a crude triethylenediamine reaction product mixture.

2. Description of the Prior Art

Triethylenediamine (TEDA) is a valuable commercial product, particularly useful as an accelerator or catalyst in conventional urethane systems employing a wide variety of isocyanates and polyols as reactants. Several methods for preparing triethylenediamine are well known. For example, one process is described by O. Hromatka et al. in Berichter Volume 76, pages 712–717 (1943) wherein triethylenediamine is obtained by the process of heating the dihydrochloride of N-(2-hydroxyethyl)piperazine. Another process involves the gaseous phase cyclization of N-hydroxyethylpiperazine vapor in the presence of a solid acid catalyst. Another well-known process is described in U.S. Pat. No. 3,080,371 to Spielberger et al which includes the liquid phase process of heating N-(2-hydroxyethyl)piperazine in the presence of a mono- or dicarboxylic acid catalyst at a temperature of from about 230° to about 350° C.

Generally, such well-known processes result in the formation of crude reaction product mixtures containing the triethylenediamine, water, by-products such as piperazine and high molecular weight polymers, as well as catalyst and solvents, if any are employed. Triethylenediamine is normally distilled from the crude reaction product by fractional distillation followed by one or more crystallization steps. The substantially pure solid triethylenediamine thus recovered is then dissolved in a suitable solvent for use as a urethane catalyst.

These generally described conventional techniques for recovering triethylenediamine have several disadvantages. Pure triethylenediamine has a freezing point of 159.8° C. and a boiling point of 174° C. Pure triethylenediamine thus is normally a liquid over a very narrow temperature range of 14.2° C. In view of this fact, it is extremely difficult to separate triethylenediamine from its crude reaction product mixtures by conventional techniques other than by crystallization. For example, pure triethylenediamine cannot be readily separated from reaction mixtures by conventional distillation techniques Further, triethylenediamine readily freezes in the distillation equipment including condensation apparatus, vent lines, and the like, causing an equipment blockage problem. Solid e.g. crystallized, triethylenediamine is also somewhat difficult to work with. For example, the crystalline material tends to cake. Further, the solid compound has a slight odor requiring the use of special handling equipment in some cases.

In as much as conventional urethane systems normally utilize liquid reaction components and the solid triethylenediamine is difficult to handle, and store the solid is normally dissolved in a suitable solvent such as an ether glycol which is compatible with urethane systems. Such triethylenediamine solutions have been prepared in a number of ways. For example, a substantially pure solid triethylenediamine may be obtained by the methods previously described herein and then dissolved in a suitable solvent. Such technique has the disadvantages as just described, particularly involving the need for crystallization and for handling a solid triethylenediamine.

SUMMARY OF THE INVENTION

In accordance with the broader aspects of the invention, a process has been devised to purify a crude triethylenediamine reaction product mixture. In essence, the crude triethylenediamine is mixed with a lower alkylene diol and then heated at ambient pressure or under vacuum to remove water and other low boiling impurities. The bottom fractions of the triethylenediamine and diol is then codistilled to produce a substantially pure triethylenediamine dissolved in liquid diol solution free of high boiling impurities. Again, the final distillation may be carried out at atmospheric conditions or under vacuum.

In a preferred embodiment a crude aqueous triethylenediamine liquid reaction mixture is obtained by heating N-hydroxyethylpiperazine in the presence of a carboxylic acid to a temperature ranging from about 230° to 350° C., more preferably 240°–270° C. and adding water to the crude reaction effluent obtained therefrom. Diol is then admixed with the crude aqueous mixture and the process of purification carried out as above.

DETAILED DESCRIPTION OF THE PREFERRED EMBODIMENTS

According to a preferred process, substantially pure triethylenediamine (TEDA) is recovered directly from a crude aqueous triethylenediamine liquid reaction mixture as a solute in a liquid diol solution. The liquid solution can thereafter be used directly to catalyze urethane systems.

Preferably the crude triethylenediamine reaction effluent is obtained by initially charging a heated reaction kettle fitted with agitation apparatus and a distillation column with N-(2-hydroxyethyl)piperazine (HEP) and a carboxylic acid catalyst. The liquid phase reaction is carried out by well known methods, for example, those disclosed in U.S. Pat. No. 3,080,371.

The crude triethylenediamine reaction effluent thus obtained is collected in an appropriate vessel with sufficient water added thereto to produce a crude aqueous liquid TEDA reactant mixture containing preferably 50–85% water. To the aqueous mixture is added a lower alkylene diol in an amount sufficient to provide a solution which contains 10–30% by weight TEDA. Water and lower boiling components are then distilled off either at ambient pressure or under vacuum. Temperature of distillation in a continuous process may range from 35° to 230° C. at 50–760 mm Hg pressure.

In a greatly preferred embodiment prior to addition of diol the crude aqueous TEDA mixture is heated to partially remove water and other impurities. The remainder of these are then taken off after diol is added.

The lower alkylene diol employed here has a structure, $HO(CH_2)_nOH$ where $n=2$ to 4. Greatly preferred is 1,4-butane-diol.

The admixture of diol and crude TEDA remaining is then codistilled by employing conventional distillation techniques and equipment. Preferably, the distillation is carried out continuously by employing a plurality of distillation columns. After the distillation has started crude TEDA/diol feed may be added to the distillation pot at a rate about equal to mixture taken off overhead. The distillation is best carried out under vacuum, say 5-150 mm Hg at a temperature range of 150°-220° C. However, the distillation of product may be effected broadly at 10-760 mm hg pressure and at 65°-220° C.

The triethylenediamine solution thus prepared contains substantially pure triethylenediamine which is present substantially as a solute of the diol solution. The triethylenediamine solution is substantially free of reaction by-product and can be used directly to catalyze urethane systems. The triethylenediamine thus recovered is not in the crystal or solid form, thus substantially reducing the problems of handling, previously encountered.

In carrying out the process of the invention, water may be added to the crude triethylenediamine effluent to produce a crude aqueous liquid triethylenediamine reaction product mixture. The addition of water is not critical to carrying out the process of the instant invention, but, is added primarily as a diluent and/or solvent. Since TEDA is soluble in water, the aqueous crude reaction product mixture is more easily handled and transferred at lower temperatures without encountering freezing or precipitation of the dissolved TEDA.

The process of the invention can be employed to recover substantially pure triethylenediamine solutions directly from crude triethylenediamine reaction product reaction mixtures obtained by practically any known liquid phase process for the preparation of triethylenediamine.

The process of the instant invention may also be employed to recover TEDA solutions from a crude liquified reaction product of known vapor phase preparation procedures. However, most vapor phase procedures for producing triethylenediamine form by-products which have a boiling point in a range such that codistillation in accordance with the present invention may not produce a TEDA solution free of by-products. Therefore, in order to practice the instant invention, the vapor phase reaction products could require removal of the similar boiling impurities, prior to the addition of diol.

The process of the invention is further disclosed in the following examples, which are meant to be illustrative but not limitative thereof.

EXAMPLE I

To a three liter three neck flask equipped with a 14" Goodloe packed column, distillation head, addition funnel and thermometer was charged 2647 g of a crude aqueous TEDA (Water 64.3%; TEDA 34.7%; piperazine, 0.5%; hydroxyethylpiperazine 0.15% and traces of decene and Dowtherm A). After taking the bulk of water, 1620 g, overhead by distillation 1,4-butanediol, 1400 g, was added to the pot. The remaining water was distilled until the head temperature rose to about 120° C. The bottoms product was cooled to 50° C.

In a 500 ml three neck flask equipped with a 14" Goodloe packed column, distillation head, thermometer and addition funnel, 1,4-butanediol 304 g was brought to reflux at 90 mm Hg pressure. After taking a small forecut, 30.0 g the above prepared crude TEDA/butanediol was fed to the pot at a rate matching that of the overhead production. Distillation continued after all the feed was added. When pot temperature reached 180° C., the distillation was stopped. By then an essentially colorless overhead product, 2536 g was present consisting of TEDA, 34.7%; 1,4-butanediol, 64.8%; traces of water, piperazine and hydroxyethylpiperazine.

The solutions of TEDA in diol produced here are essentially colorless. In addition, the process was so designed that no plugging of solid TEDA in distillation equipment was observed.

Obviously, many modifications and variations of the invention are set forth may be made without departing from the spirit and scope thereof, and therefore, only such limitations should be imposed as are indicated in the appended claims.

We claim:
1. An improved process for directly recovering a substantially pure triethylenediamine solute in a 1,4-butanediol solution from a crude aqueous triethylenediamine reaction product mixture obtained from a liquid phase process for the preparation of triethylenediamine comprising the steps of admixing said 1,4-butanediol with said crude triethylenediamine reaction product mixture to form a crude triethylenediamine reaction product-1,4-butanediol admixture; heating said admixture under conditions such that water and other lower boiling impurities are removed and heating the resultant bottoms to produce a codistillate of a substantially pure triethylenediamine solute in liquid 1,4-butanediol solution.

* * * * *